United States Patent
Subbiah et al.

(12) 
(10) Patent No.: US 6,365,411 B1
(45) Date of Patent: Apr. 2, 2002

(54) RAIN FOREST PLANT EXTRACT WITH CELLULAR CHOLESTEROL LOWERING PROPERTIES

(75) Inventors: M. T. Ravi Subbiah; Eric J. Norman, both of Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/589,490

(22) Filed: Jun. 7, 2000

Related U.S. Application Data

(60) Provisional application No. 60/138,396, filed on Jun. 9, 1999.

(51) Int. Cl.⁷ .................. A61K 35/78; A01N 65/00
(52) U.S. Cl. ............................ 435/725; 424/774
(58) Field of Search ................. 424/725, 774

(56) References Cited

U.S. PATENT DOCUMENTS 4,623,662 A   11/1986   DeVries ............... 514/596
4,722,927 A   2/1988   Holmes ................ 514/256

OTHER PUBLICATIONS

Cayatte AC, Kumbla L, and Subbiah MTR. J Biol Chem 265:5883–5888 (1990).

Arai H, Kita T, Yokodo M, Narumiya S, and Kawai C. Biochem Biophys Res Commun 159:1375 (1989).

Bhadra S, Arshad MAQ, Rymaszewski Z, Norman E, and Subbiah MTR. Bioehem Biophys Res Commun 176:431–440 (1991).

*Primary Examiner*—Herbert J. Lilling
(74) *Attorney, Agent, or Firm*—Frost Brown Todd LLC

(57) ABSTRACT

In the rain forest region of Karnataka State, India, a scandent herb Justicia known as "medicine plant" is widely consumed by the local population by incorporating its extract into desserts. This is especially common in the months of June through August because of the belief that the medicinal properties reach their peak during this season. This plant is now considered to be distributed exclusively in this region of the South Indian rain forest. The plant extract lowers cellular cholesterol and cholesteryl ester concentration. Further studies also showed a novel inhibitory effect on the uptake of ox-LDL by human macrophage cell line.

21 Claims, 1 Drawing Sheet

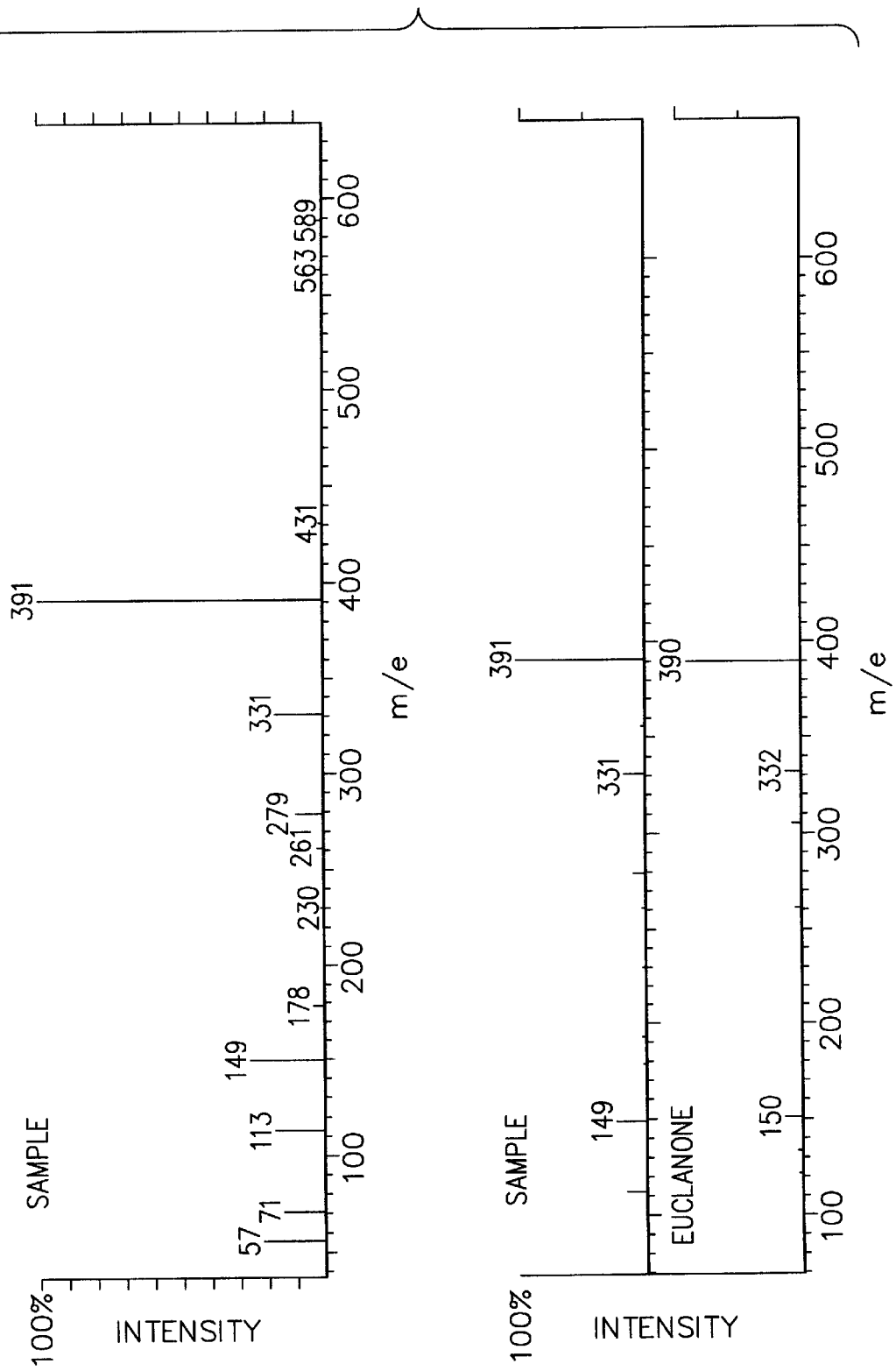

RAIN FOREST PLANT EXTRACT WITH CELLULAR CHOLESTEROL LOWERING PROPERTIES

This application claims benefit to earlier filed Provisional No. 60/138,396 Jun. 9, 1999.

FIELD OF THE INVENTION

The present invention relates to plant extracts and the use of plant extracts for medicinal purposes. More specifically, the present invention relates to Justicia plant extracts and their use for lowering cellular cholesterol and cholesteryl ester concentration. This invention relates to the preparation by thin-layer chromatographic fractionation of an ethanolic extract from the leaves of the plant Justicia and preferably from the species *Justicia wynaadensis* ("WJ") which possesses biological activity, and the use of such extracts for the treatment of hypercholesterolemia and atherosclerosis.

DESCRIPTION OF THE RELATED ART

Hypercholesterolemia is an established risk factor in the development of atherosclerosis. Therapeutic agents which control the level of serum cholesterol have proven to be effective in the treatment of coronary artery disease. While agents exist that can modulate circulating levels of cholesterol carrying lipoproteins by inhibiting cholesterol synthesis, these agents have little or no effect on the intestinal absorption of cholesterol. Dietary cholesterol can increase the level of serum cholesterol to levels which place an individual at increased risk for the development or exacerbation of atherosclerosis.

The liver has a central role in the storage, synthesis, and metabolic transformations of lipids. One major function of the liver is to package triglycerides and cholesterol, which are insoluble in plasma, into particles called lipoproteins which can be carried in the bloodstream. The liver both secretes lipoproteins and also reabsorbs them after they have exchanged their lipid loads with peripheral tissues.

Four major classes of lipoproteins are known. All have an "oildrop" core of neutral lipid (triglycerides and/or cholesteryl esters) surrounded by an amphiphilic surface layer of phospholipids, cholesterol, and apolipoproteins. The larger the "oildrop" core, the less dense is the lipoprotein particle. In decreasing order of size, the four classes are: (a) chylomicrons, which are secreted by the small intestine rather than the liver, and consist mostly of triglycerides absorbed from dietary fat; (b) very low density lipoproteins (VLDLs), which are secreted by the liver and contain mostly triglycerides; (c) low density lipoproteins (LDLs), which are generated in the liver from VLDL remnants, and contain mostly cholesteryl esters rather than triglycerides; and (d) high density lipoproteins (HDLs), which are secreted by the liver as phospholipid-rich discoidal particles, but which develop a lipid core by scavenging cholesterol from peripheral tissues.

Atherosclerosis weakens the arterial wall and narrows the flow path of blood within the vessels. Atherosclerotic lesions frequently appear in particular in the coronary arteries, producing coronary heart disease. As the plaque increases in size, the coronary arteries may become completely blocked; when that occurs, the heart muscles are deprived of oxygen from the blood and the victim suffers a "heart attack", or myocardial infarction.

The risk of coronary heart disease increases dramatically as the plasma concentration of LDL cholesterol increases. Consequently, development of methods for lowering LDL cholesterol levels has become a major focus of medical research. The straightforward approach of reducing dietary cholesterol intake suffers from two limitations. The first is that cholesterol is present in all animal fats, and many Americans are unwilling to sacrifice their preferred diet. The second is that the liver and other tissues synthesize cholesterol de novo if the dietary supply is inadequate.

Cholesterol is an essential component of cellular membranes as well as a necessary precursor of metabolically important compounds such as bile acids and steroids. Cells obtain their necessary complement of cholesterol by taking up LDL particles through a specialized LDL receptor. The activity of the LDL receptors varies according to the cell's need for more cholesterol. Both peripheral cells and liver cells take up LDL through the receptor mechanism. However, unlike other cells, liver cells can both secrete and metabolically transform cholesterol, thereby removing it from the body. Thus when LDL receptor activity is low, the plasma LDL cholesterol level may be expected to rise, because LDL particles are not being removed from circulation as quickly as they are produced from VLDL remnants. This effect is accentuated by the fact that the liver removes VLDL remnants from circulation via the same LDL receptor; when LDL receptor activity is low, a smaller fraction of VLDL remnants is degraded, and consequently more remnants are converted into LDL particles instead. LDL receptor down-regulation thus decreases LDL clearance at the same time that the rate of LDL particle generation is increased. The result of this dual mechanism is that cholesterol levels climb markedly when LDL receptor activity decreases. It is thus believed that the ability to lower cellular cholesterol and cholesteryl esterase levels would be of great benefit in reducing the adverse effects of hypercholesterolemia. This is especially important in blood cells (monocytes) and in cells that line the blood vessels.

A number of patents in the literature disclose compounds which are useful as anti-atherosclerotic agents in general. For example, U.S. Pat. No. 4,623,662, issued De Vries on Nov. 18, 1986, discloses ureas and thioureas as ACAT inhibitors useful for reducing the cholesterol ester content of an arterial wall, inhibiting atherosclerotic lesion development, and/or treatment of mammalian hyperlipidemia. U.S. Pat. No. 4,722,927, issued to Holmes on Feb. 2, 1988, discloses disubstituted pyrimidineamides of oleic and linoleic acids as ACAT inhibitors useful for inhibiting intestinal absorption of cholesterol.

In the rain forest region of Karnataka State, India, a scandent herb Justicia Wynaadensis ("JW") known as "medicine plant" is widely consumed by the local population by incorporating its extract into desserts. This seasonal plant is believed by the local tribes to possess healing properties. The extracts of the leaves are consumed for the treatment of a variety of diseases. This is especially common in the months of June through August because of the belief that the medicinal properties reach their peak during this season. This plant is now considered to be distributed exclusively in this region of the South Indian rain forest.

However, nothing is known regarding the pharmacology or biochemistry of this plant, except that upon ingestion a purple-colored urine is noticed. In addition, there are no known literature references disclosing the extracts of this plant or their use to lower cholesterol or in the treatment of atherosclerosis.

The plant extracts of the present invention lower cellular cholesterol and cholesteryl ester concentration. In view of its rich color (bluish purple), pleasant aroma, and years of consumption by the local population its potential as a food supplement with cellular cholesterol lowering properties deserves attention.

SUMMARY OF THE INVENTION

It is therefore an object of the present invention to a method of producing a new active compound for lowering cellular cholesterol levels.

It is another object of the present invention to provide an industrially feasible method of producing aforementioned extract.

The above objects are achieved by the present invention which was completed on the basis of the discovery by the present inventor that the Justicia extract is capable of lowering cellular cholesterol. Specifically, the present invention relates to a method for preparing a composition capable of lowering cellular cholesterol and cholesteryl ester concentration comprising the steps of: preparing an aqueous extract of dried and powdered leaves of the plant Justicia by adding about 10 parts by weight of said leaves to about 90 parts by weight of about 95% water-miscible alcohol at room temperature for a time sufficient to complete dissolution, centrifuging and filtering the solution; subjecting said alcoholic extract to thin-layer chromatographic fractionation on 250 μm silica gel G plates in a solvent consisting essentially of chloroform:methanol:water (60:40:10, v/v/v); to obtain a fraction from the first band having an RF value of about 0.80 to about 0.85 as defined herein; separating and dissolving said fraction obtained from the first band.

The invention encompasses pharmaceutical compositions which incorporate the active component prepared by the disclosed methods.

BRIEF DESCRIPTION OF THE FIGURE

FIG. 1. This FIGURE shows the mass spectrum of one of the components of the Justicia extract.

DETAILED DESCRIPTION OF THE INVENTION

In the rain forest region of South India, a seasonal plant known as "medicine plant" is believed by the local tribes to possess healing properties. The extracts of the leaves are consumed for a variety of diseases. Nothing is known regarding the pharmacology or biochemistry of this plant, except that upon ingestion a purple-colored urine is noticed.

The plant extract possesses the following properties: it lowers cellular cholesterol and cholesteryl ester concentration. While searching for mechanisms in murine macrophages, it was noticed that the extract counteracted the rise in cholesterol (especially free cholesterol) in response to oxidized LDL, a step considered to be critical in the initiation of atherogenic events. Further studies also showed a novel inhibitory effect on the uptake of ox-LDL by human macrophage cell line. In view of its rich color (bluish purple), pleasant aroma, and years of consumption by the local population its potential as a food supplement with cellular cholesterol lowering properties deserves attention.

The present invention discloses a method of producing a plant extract characterized in that the extract lowers cellular cholesterol levels. The extract is obtained by extraction of a *Justicia Linnaeus* genus of plants and is preferably obtained from the *Justicia wynaadensis* ("JW") plant. It has been found that a wide variety of extraction solvents can be used to obtain extracts of these plant species having cholesterol-lowering activity. This species is also known as *Gendarussa wynaadensis* and *Adhatoda wynaadensis*. The following species fall under the genus *Justicia sensu lato: J. japonica, J. procumbens, J. glabra, J. wynaadensis, J. betonica*, and *J santapaui*.

Extracts of the subject invention may be obtained from a variety of tissues from the above-identified plant species. Extracts from the above-ground tissues of the-plants are preferred, especially from the leaves. Extracts may be made from fresh plant tissues, or from the tissues after they are dried. Preferred are extracts of dried leaves.

As used herein, "extracting" or "extraction" of a solid or liquid material means contacting the material, which if solid is preferably dried and crushed or ground, with an appropriate solvent to remove the substance(s) desired to be extracted from the material. Such an extraction may be carried out by conventional means; for example, by using an extraction apparatus, such as a Soxhlet apparatus, which retains the solid material in a holder and allows the solvent to flow through the material; or by blending the solvent and material together and then separating the liquid and solid phases or two immiscible liquid phases, such as by filtration or by settling and decanting.

"Treatment" covers any treatment of the disease in a mammal, particularly human, and includes: (i) preventing the disease from occurring in a subject which may be predisposed to the disease but has not yet been diagnosed as having it; (ii) inhibiting the disease, i.e. arresting the development of said disease; or (iii) relieving the disease, i.e. causing regression of the disease.

"Hypercholesterolemia" also known as hypercholesteremia or hypercholesterinemia, means the presence of an abnormally large amount of cholesterol in the cells and plasma of the circulating blood.

"Arteriosclerosis" as used herein means a degenerative arterial sclerosis marked by hardening and thickening of the vessel walls.

As used herein, "an effective amount" of a composition is that amount that, when administered to a subject, results in a decrease in cellular cholesterol and cholesteryl ester concentration. As used herein, "a safe and effective amount" of a composition is that amount which is pharmaceutically safe to a subject and that causes a decrease in cellular cholesterol and cholesteryl ester concentration while causing no side effects or an acceptable level of side effects.

An alcoholic extract of the leaves was screened for: a) antiplatelet aggregatory activity, b) antioxidant activity, and c) cholesterol metabolic activity in cell cultures. No antioxidant or antiplatelet aggregatory activity was noted. Initial studies demonstrated that the extract was effective in decreasing cholesterol and cholesterol ester concentrations in cultured human skin fibroblasts and murine macrophages. While searching for mechanisms, one of the interesting observations made was that the extract was very effective in counteracting the rise in cellular cholesterol in response to oxidized LDL. This indicated that the extract might inhibit either the binding or further processing of ox-LDL by macrophages, a step considered to be critical in the initiation of atherogenic events. Studies carried out on this plant extract with regard to cholesterol metabolism are disclosed. Studies carried out on this plant extract with regard to cholesterol metabolism are discussed. In view of its rich color and aroma and years of consumption by the local population, this extract possesses potential for development as a food supplement.

Leaves of the Justicia plants are obtained from the rain forest region of South India. The first step is in preparing an aqueous extract of dried and powdered leaves of the plant Justicia by adding about 10 parts by weight of said leaves to about 90 parts by weight of about 95% water-miscible alcohol at room temperature for a time sufficient to complete dissolution, centrifuging and filtering the solution. The water-miscible alcoholic extracts are concentrated into smaller volumes and initially fractionated by TLC or silica gel using the solvent system chloroform:methanol:water (typically about 60:40:10, v/v/v). Most of the activity is confined to the region near the solvent front. The material from the solvent front band with Rf values from about 0.70 to about 1.00 is collected. Preferably, the material from the solvent front band with Rf values from about 0.80 to about 0.90 is collected and most preferably the material from the solvent front band with Rf values from about 0.80 to about 0.85 is collected. This band is eluted with about 5 ml of water-miscible alcohol and then concentrated to a small volume and used for the experiments.

The fraction taken from the solvent front or the first silica gel chromatography, (fraction "0"), is further purified by a second thin layer chromatography on silica gel G using a solvent system Heptane:lsopropyl Ether:Acetic Acid (60:40:4, v/v/v). In this system, five bands are obtained on the silica gel. These bands have Rf values (distance band moved from origin/distance the solvent front moved from the origin) of:

TABLE 1

Fractions Obtained From Second Chromatography

| Band No. | Rf Value |
| --- | --- |
| Fraction 1 | from about 0.80 to about 0.85 |
| Fraction 2 | from about 0.70 to about 0.75 |
| Fraction 3 | from about 0.55 to about 0.65 |
| Fraction 4 | from about 0.30 to about 0.40 |
| Fraction 5 | from about 0.20 to about 0.25 |

Each of the bands is eluted with about 5 ml of water-miscible alcohol and then concentrated to a small volume and used for the experiments.

The subject invention includes a process for preparing an alcohol extract of tissues of the plants of interest, preferably of leaves, especially dried leaves, by extracting the tissues using water-miscible alcohol, such as methanol, ethanol, n-propanol or iso-propanol or mixtures of such alcohols with up to about 50% water; the preferred alcohol is ethanol. Preferably, 1 part of plant tissues (dry basis) is extracted with from about 5 to about 50 parts, more preferably from about 8 to about 25 parts of solvent, using an extraction apparatus, where the solvent is refluxed through the tissues, for a period of from about 4 to about 48 hours, preferably for from about 12 to about 24 hours. The alcohol is preferably evaporated from the resulting liquid alcohol extract, that providing a solid alcohol extract.

Alternatively, the extract may obtained by using an extracting solution of a water-miscible alcohol or a water-miscible alcohol/i-butanol mixture.

The effect of fractions on cholesterol esterification (using $C^{14}$-oleic acid) and cholesterol (free and ester) content of the cells was evaluated as described previously (Cayatte A C, Kumbla L, and Subbiah M T R. J Biol Chem 265:5883–5888, (1990)). The effect of active fractions of the extract on the binding and uptake of $^{125}I$-ox-LDL were examined by the methods described by Arai, et al (Arai H, Kita T, Yokodo M, Narumiya S, and Kawai C. Biochem Biophys Res Commun 159:1375 (1989)). GC/MS analyses were carried out initially as described previously (Bhadra S, Arshad MAQ, Rymaszewski Z, Norman E, and Subbiah M T R. Bioehem Biophys Res Commun 176:431–440 (1991)) using a GC/MS equipped with a capillary column (30 meter, DB-5, 0.25 mm micron film thickness 0.25 mm ID, J&W Scientific Co., Folsom, Calif.).

Studies of the Activity of the Extracts

Preliminary studies of Fractions 3 and 4, which are active, were subjected to GC/MS analysis using the column condition described (Bhadra S, Arshad MAQ, Rymaszewski Z, Norman E, and Subbiah M T R. Bioehem Biophys Res Commun 176:431–440 (1991)) for sterols. Several peaks with retention times (8.65–11.40) were noted. The mass spectrum of one of the compounds matched by library search with a compound known as Euclanone (FIG. 1) with a molecular weight of 392. In view of the color exhibited by these compounds it appears that they may be derivatives of naphthoquinone dimer like compounds, perhaps containing 7-methyl juglone units (a component of Euclanone). Electrospray mass spectrometry indicated a number of compounds, a predominant one with a molecular weight of 359.

The compound isolated after ethanolic extraction of this plant may be used in the form of syrups, extracts and distillates as flavoring agents or food additives and supplements.

The compounds of the invention may be employed in the treatment of high serum cholesterol in mammals, by formulating compositions of pharmaceutically suitable carriers known in the art with various compounds of the invention in amounts effective to lower cellular cholesterol and cholesteryl ester concentration.

It is contemplated that such target cells may be located within an animal or human patient, in which case a safe and effective amount of the complex, in pharmacologically acceptable form, would be administered to the patient. Generally speaking, it is contemplated that useful pharmaceutical compositions of the present invention will include the selected extracts in a convenient amount, e.g., from about 1% to about 90% (w/w) that is diluted in a pharmacologically or physiologically acceptable carrier, such as, for example, phosphate buffered saline. The route of administration and ultimate amount of material that is administered to the patient or animal under such circumstances will depend upon the intended application and will be apparent to those of skill in the art in light of the examples which follow.

The composition can comprise, in addition to the extract, compounds and/or compositions that will also aid in relief of the symptoms of hypercholesterolemia, such as anti-atherosclerotic agents (e.g., ACAT inhibitors) or complementary drugs and hormones, in dosages useful for relief of the symptoms of hypercholesterolemia, as known to those skilled in the art. Dosages for the above-mentioned additional compounds are established and known to those skilled in the art. The ratio of extract to additional agent is dependent upon the dose desired of each individual compound. Preferably, the additional agent will be administered as a pharmaceutically acceptable solution or powder.

The compound useful in the present inventive method may be administered by any suitable means. One skilled in the art will appreciate that many suitable methods of administering the extract to an animal in the context of the present invention, in particular a human, are available, and, although more than one route may be used to administer the extract, a particular route of administration may provide a more immediate and more effective reaction than another route. The preferred methods utilize oral administration to a subject. In addition to standard pharmaceutical administration, the extract prepared by the methods of the present invention are useful as a food supplement.

The compound should be administered such that a therapeutically effective concentration of the compound is in contact with the affected cells of the body. The dose administered to an animal, particularly a human, in the context of the present invention should be sufficient to effect a therapeutic response in the animal over a reasonable period of time. The dose will be determined by the strength of the particular compound employed and the condition of the animal, as well as the body weight of the animal to be treated. The size of the dose also will be determined by the existence, nature, and extent of any adverse side effects that might accompany the administration of the extract and the particular route of administration employed with a particular patient.

Another aspect of the subject invention involves compositions comprising an extract of the subject invention, such as described hereinabove, and a pharmaceutically-acceptable carrier. Preferred compositions are those in dosage forms intended for oral administration. Fluid dosage forms for oral administration include solutions, suspensions, emulsions, and the like. Solid dosage forms for oral administration include tablets, capsules, powders, lozenges, and the like.

The term "pharmaceutically-acceptable carrier" as used herein means one or more compatible solid or liquid filler diluent or encapsulating substance which is suitable for administration to a human or lower animal. The term "compatible" as used herein means that the components of the pharmaceutical carrier are capable of being commingled with the extracts of the subject invention, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

The methods of the subject invention include treatment of humans and lower animals, especially humans, currently suffering from one or more elevated cholesterol disorder, particularly those specified herein, in order to reduce the severity of the disorder. The methods of the subject invention also include the prevention of high cholesterol disorders in humans and lower animals, especially humans, having a propensity for such disorders, particularly those specified herein, by prophylactic treatment in order to prevent occurrence of the disorder.

The methods of the subject invention include administering to a human or lower animal a composition comprising an extract of the subject invention. The quantity of extract (dry basis) administered is preferably from about 1 mg/kg to about 1000 mg/kg, preferably from about 5 mg/kg to about 500 mg/kg, and more preferably still from about 10 mg/kg to about 200 mg/kg, from about 1 to about 4 times a day.

The compound may be administered in combination with a pharmaceutically acceptable carrier. Pharmaceutically acceptable carriers are well-known to those who are skilled in the art. The choice of carrier will be determined in part by the particular compound, as well as by the particular method used to administer the composition. Accordingly, there is a wide variety of suitable formulations of the pharmaceutical composition of the present invention.

Formulations suitable for oral administration include (a) liquid solutions, such as an effective amount of the compound dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms may include, for example, one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels and the like containing, in addition to the active ingredient, such carriers as are known in the art.

Formulations suitable for intravenous and intraperitoneal administration, for example, include aqueous and nonaqueous, isotonic sterile injection solutions, which can contain anti-oxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carriers for example, water, for injections, immediately prior to use. Extemporaneous injection solutions and suspensions can be prepared for sterile powders, granules, and tablets of the kind previously described.

The exact amount of such compounds required will vary from subject to subject, depending on the species, age, and general condition of the subject, the severity of the disease that is being treated, the particular extract used, its mode of administration, and the like. Thus, it is not possible to specify an exact activity promoting amount. However, an appropriate amount may be determined by one of ordinary skill in the art using only routine testing given the teachings herein.

EXAMPLES

Example 1

Effect of WJ Extracts on Cholesterol and Cholesterol Ester Content in Murine J-774 Macrophages Murine macrophages were incubated with WJ extract (10 $\mu$l/ml) in the absence or presence of LDL isolated as described (Kumbla L, Bhadra S, and Subbiah M T R. FASEB J 5:2971–2975 (1991) (250 $\mu$g/ml) or ox-LDL (125 $\mu$g/ml) for 48 hours. The content of cholesterol and cholesterol ester were measured following extraction and GLC (Table 2).

WJ extract markedly reduced both free and esterified cholesterol content of the cells. The extract also exhibited a mild ability to inhibit cholesterol esterification using techniques used previously (Cayatte A C, Kumbla L, and Subbiah M T R. J Biol Chem 265:5883–5888, (1990)); Kemper H J M, Vermeer M, de Witt E, and Havekines L M. Arterioscler Thromb 11:146, (1991)).

TABLE 2

Effect of WJ Extract On Cholesterol and Cholestrerol ester Content of Murine Macrophages

| Groups | Free Cholesterol (ug/mg P) | Cholesterol Ester (ug/mg P) | Total Cholesterol (ug/mg P) |
|---|---|---|---|
| Control | 14.31 + 7.0 | 0.65 + 0.27 | 14.96 + 7.27 |
| LDL | 28.12 + 8.5 | 7.28 ± 1.7 | 35.40 ± 11.2 |
| LDL + WJ | 4.11 ± 0.75$^a$ | 4.99 ± 1.3$^c$ | 9.1 ± 2.0$^d$ |
| ox-LDL | 35.86 ± 2.69 | 8.57 ± 0.72 | 44.43 ± 3.41 |
| ox-LDL + WJ | 6.92 ± 1.69$^b$ | 5.95 ± 2.7 | 12.51 ± 4.3$^d$ |

$^{a,b,c,d}p < 0.05$ for difference from respective controls

Example 3
Effect of WJ Extract on the Incorporation of 3H-cholestrerol Oleate into THP-I Macrophage Cell Line Labeled $^3$H-cholestrerol oleate was added to a medium (RPMI/HEPES) with 1% serum and incubated with THP-I cells) 1.5 ml/well) for 4, 48, and 72 hours in the presence and absence of WJ extract (5 ul/ml). After various times the media was aspirated and cells washed twice with 1 ml cold PBS (phosphate buffered saline). The cells were extracted with ethanol, the extracts were fractionated by TLC to separate free and esterified cholesterol. The amount of radioactivity in each fraction was assessed by scintillation counting and expressed as c.p.m/ng DNA×$10^{-3}$.

TABLE 3

Incorporation of $^3$H-Cholestrerol Oleate into THP-1 Macrophage Cell Line: Effect of WJ Extract

| EXPT Group | Cholesterol Fractions | Cellular Radioactivity (c.p.m./ng DNA × $10^{-3}$) (Mean + SEM) | | |
|---|---|---|---|---|
| | | 4 hrs | 48 hrs | 72 hrs |
| Control + WJ (5 ul/ml) | Free | 203 + 6 102 ± 7* | 3217 ± 208 1813 ± 145* | 2578 ± 46 1541 ± 236* |
| Control + WJ (5 ul/ml) | Ester | 3315 ± 40 2463 ± 99* | 2539 ± 199 3767 ± 248 | 2245 ± 324 4715 ± 552 |
| Control + WJ (5 ul/ml) | Total | 3522 ± 47* 2565 ± 183 | 5756 ± 407 5580 ± 373 | 4824 ± 324 6256 ± 778 |

*p < 0.05 for difference from respective controls.

These results show that at all time points the accumulation of free cholesterol is significantly less in WJ treated fractions. The amount of cholesterol esters and total cholesterol is also significantly less at 4 hours. The cholesterol ester fractions at 48 and 72 hours increased slightly.

Example 3
Effects of WJ Extract on the Binding and Degradation of $^{125}$I Labeled-ox-LDL by THP-I Cells THP-I cells were kept on lipoprotein deficient serum for 24 hours before carrying out binding experiments. $^{125}$I-ox-LDL (10 ug/ml) was incubated with cells at 4° C. for 60 minutes. The medium W3S then taken for the measurement of heparin releasable $^{125}$I-ox-LDL that was bound to the cells. The cells were incubated with 0.1 N KOH overnight and protein content and radioactivity were measured. To determine degradation of $^{125}$I-ox-LDL (10 ug/ml), the cells were incubated at 37° C. for one hour. The medium was removed and proteins precipitated with cold TCA. About 0.5 ml of filtrate was treated with 0.25 ml of 5% AgNO$_3$, spun, and 200 ul taken for counting cell homogenates were used for protein measurement. The amount of $^{125}$I-ox-LDL degraded was then assessed.

The results clearly show that the WJ extract interferes with the binding and subsequent degradation of $^{125}$I-ox-LDL by macrophages.

TABLE 4

Binding and Degradation of $^{125}$I-ox-LDL by THP-1 Macrophages: Effect of WJ Extract

| EXPT Group | $^{125}$I-ox-LDL Binding (HR) (ug/mg Protein) (Mean ± SEM) | $^{125}$I-ox-LDL Degraded (ug/mg Protein) (Mean ± SEM) |
|---|---|---|
| Control | 40.1 ± 1.5 | 3021 ± 69 |
| + WJ (2 ul/ml) | 30.5 ± 2.5** | 2693 ± 57** |
| + WJ (5 ul/ml) | 26.0 ± 1.9** | 2475 ± 69** |

*heparin releasable binding
**p < 0.05 when compared to controls

I claim:

1. A composition capable of lowering cellular cholesterol and cholesteryl ester concentration comprising a fraction which is isolated from Justicia by extraction with a water-miscible alcohol, said fraction being characterized in that it: has cholesterol level inhibiting activity; gives a positive color test with vanillin/sulfuric acid reagent and concentrated hydrochloric acid reagent; and has an Rf value between about 0.7 to about 1.0 when subjected to thin-layer chromatographic fractionation on 250 μm silica gel G plates eluted with a solvent consisting essentially of chloroform:methanol:water (60:40:10, v/v/v).

2. The composition of claim 1, wherein said fraction has an Rf value between about about 0.80 to about 0.90.

3. The composition of claim 1, wherein said Justicia plant is the plant Justicia Wynaadensis.

4. A method of preparing a composition capable of lowering cellular cholesterol and cholesteryl ester concentration, comprising the steps of: (a) preparing an water-miscible alcohol extract of leaves of the plant Justicia by adding about 10 parts by weight of said leaves to about 90 parts by weight 95% a water-miscible alcohol at room temperature for a time sufficient to complete dissolution, (b) centrifuging and filtering the solution; (c) subjecting said a water-miscible alcohol extract to thin-layer chromatographic fractionation on 250 μm silica gel G plates in a solvent consisting essentially of chloroform:methanol:water (60:40:10, v/v/v); and (d) collecting a fraction from the first band having an RF value of about 0.7 to about 1.0 as defined herein.

5. The method of claim 4, wherein said fraction collected has an Rf value between about 0.80 to about 0.90.

6. The method of claim 4, wherein said fraction collected has an Rf value between about 0.80 to about 0.85.

7. The method of claim 4, wherein said Justicia plant is the plant Justicia Wynaadensis.

8. The method of claim 4, wherein said fraction collected from the first band is further subjected to thin-layer chromatographic fractionation on 250 μm silica gel G plates in a solvent consisting essentially of Heptane:lsopropyl Ether:Acetic Acid (60:40:4, v/v/v) to obtain a fraction having an RF value of about 0.55 to about 0.65 as defined herein.

9. The method of claim 4, wherein said fraction collected from the first band is further subjected to thin-layer chromatographic fractionation on 250 μm silica gel G plates in a solvent consisting essentially of Heptane:Isopropyl Ether:Acetic Acid (60:40:4, v/v/v) to obtain a fraction having an RF value of about 0.3 to about 0.4 as defined herein.

10. The method of claim 4, wherein said fraction collected from the first band is further subjected to thin-layer chromatographic fractionation on 250 μm silica gel G plates in a solvent consisting essentially of Heptane:lsopropyl Ether-:Acetic Acid (60:40:4, v/v/v) to obtain two fractions from the first band having RF values of from about 0.55 to about 0.65 and from about 0.30 and about 0.40 as defined herein.

11. The method of claim 4 wherein said extract is obtained by using an extracting solution selected from the group consisting of a water-miscible alcohol and a water-miscible alcohol/I-butanol mixture.

12. The method of claim 4 wherein the water-miscible alcohol is selected from the group consisting of methanol, ethanol, butanol, propanol and mixtures thereof.

13. A composition capable of lower cellular cholesterol and cholesteryl ester concentration in mammalian blood, comprising an effective amount of a centrifuged eluate having an RF value of about 0.80 to about 0.90 prepared in accordance with the method of claim 4.

14. A composition comprising from about 1% to about 95% of the composition of claim 13 and from about 5% to about 99% of a pharmaceutically-acceptable carrier.

15. A composition capable of lowering cellular cholesterol and cholesteryl ester concentration in mammalian blood, comprising an effective amount of a centrifuged eluate having an RF value of about 0.80 to about 0.85 prepared in accordance with the method of claim 4.

16. A composition comprising from about 1% to about 95% of the composition of claim 15 and from about 5% to about 99% of a pharmaceutically-acceptable carrier.

17. A method of lowering cellular cholesterol and cholesteryl ester concentration in mammalian blood, which comprises administering to a mammalian host a safe and effective amount of a centrifuged eluate having an RF value of about 0.80 to about 0.85 prepared in accordance with the method of claim 4.

18. A composition capable of lowering cellular cholesterol and cholesteryl ester concentration in mammalian blood, comprising an effective amount of a centrifuged eluate having RF values of from about 0.55 to about 0.65 and from about 0.30 and about 0.40 as defined herein prepared in accordance with the method of claim 10.

19. A composition comprising from about 1% to about 95% of the composition of claim 18 and from about 5% to about 99% of a pharmaceutically-acceptable carrier.

20. A method of lowering cellular cholesterol and cholesteryl ester concentration in mammalian blood, which comprises administering to a mammalian host a safe and effective amount of a centrifuged eluate having RF values of from about 0.55 to about 0.65 and from about 0.30 and about 0.40 as defined herein prepared in accordance with the method of claim 10.

21. A composition comprising from about 1% to about 95% of the composition of claim 20 and from about 5% to about 99% of a pharmaceutically-acceptable carrier.

* * * * *